(12) United States Patent
Van Hoeck et al.

(10) Patent No.: US 8,075,622 B2
(45) Date of Patent: *Dec. 13, 2011

(54) INTERVERTEBRAL SPACERS

(75) Inventors: James E. Van Hoeck, Cordova, TN (US); Troy McDonald, Millington, TN (US); Bradley J. Coates, Rossville, TN (US); Regis W. Haid, Jr., Atlanta, GA (US); Stephen E. Heim, Memphis, TN (US); Kevin Foley, Germantown, TN (US); Eugene C. Eckstein, Germantown, TN (US)

(73) Assignee: Warsaw Orthopedic, Inc, Warsaw, IN (US)

(*) Notice: Subject to any disclaimer, the term of this patent is extended or adjusted under 35 U.S.C. 154(b) by 635 days.

This patent is subject to a terminal disclaimer.

(21) Appl. No.: 12/004,647

(22) Filed: Dec. 21, 2007

(65) Prior Publication Data

US 2008/0109083 A1    May 8, 2008

Related U.S. Application Data

(63) Continuation of application No. 10/775,546, filed on Feb. 10, 2004, now Pat. No. 7,311,734, which is a continuation of application No. 10/201,549, filed on Jul. 23, 2002, now abandoned, which is a continuation of application No. 08/603,676, filed on Feb. 20, 1996, now Pat. No. 6,423,095, which is a continuation-in-part of application No. 08/543,563, filed on Oct. 16, 1995, now abandoned.

(51) Int. Cl.
*A61F 2/44* (2006.01)

(52) U.S. Cl. .................. 623/17.16; 623/17.11

(58) Field of Classification Search ..... 623/17.11–17.16
See application file for complete search history.

(56) References Cited

U.S. PATENT DOCUMENTS

| | | | |
|---|---|---|---|
| 3,848,601 A | 11/1974 | Ma et al. | |
| 4,309,777 A | 1/1982 | Patil | |
| 4,349,921 A | 9/1982 | Kuntz | |
| 4,501,269 A | 2/1985 | Bagby | |
| 4,526,909 A | 7/1985 | Urist | |

(Continued)

FOREIGN PATENT DOCUMENTS

EP     0 179 695     4/1986

(Continued)

OTHER PUBLICATIONS

The Anterior Approach for Removal of Ruptured Cervical Disks, Ralph B. Cloward, M.D., Honolulu Kawaii, Presented at the meeting of the Harvey Cushing Society, Washington, D.C., Apr. 22, 1958.

(Continued)

*Primary Examiner* — Todd Manahan
*Assistant Examiner* — Lynnsy Schneider

(57) ABSTRACT

One embodiment of a hollow spinal spacer (10) includes a curved anterior wall (11) having opposite ends (12, 13), a posterior wall (15) having opposite ends (16, 17), two lateral walls (20, 21), each integrally connected between the opposite ends (12, 13, 16, 17) of the anterior (11) and posterior (15) walls to define a chamber (30). The walls (11, 15, 20, 21) include a superior face (35) and an inferior face (40). The superior face (35) defines a first opening (36) in communication with the chamber (30) and includes a first vertebral engaging surface (37). The inferior face (40) defines a second opening (41) in communication with the chamber (30) and includes a second vertebral engaging surface (42).

27 Claims, 7 Drawing Sheets

U.S. PATENT DOCUMENTS

| | | | |
|---|---|---|---|
| 4,596,574 | A | 6/1986 | Urist |
| 4,599,086 | A | 7/1986 | Doty |
| 4,620,327 | A | 11/1986 | Caplan et al. |
| 4,623,553 | A | 11/1986 | Ries et al. |
| 4,703,108 | A | 10/1987 | Silver et al. |
| 4,714,469 | A | 12/1987 | Kenna |
| 4,743,256 | A | 5/1988 | Brantigan |
| 4,759,766 | A | 7/1988 | Buettner-Janz et al. |
| 4,772,287 | A | 9/1988 | Ray et al. |
| 5,015,247 | A | 5/1991 | Michelson |
| 5,147,402 | A | 9/1992 | Bohler et al. |
| 5,192,327 | A * | 3/1993 | Brantigan .................. 623/17.11 |
| 5,282,861 | A * | 2/1994 | Kaplan ....................... 623/23.51 |
| 5,306,309 | A * | 4/1994 | Wagner et al. ............. 623/17.16 |
| 5,366,875 | A | 11/1994 | Wozney et al. |
| 5,397,364 | A | 3/1995 | Kozak et al. |
| 5,425,772 | A | 6/1995 | Brantigan |
| 5,443,515 | A | 8/1995 | Cohen et al. |
| 5,514,180 | A * | 5/1996 | Heggeness et al. ......... 623/17.16 |
| 5,522,899 | A * | 6/1996 | Michelson .................... 606/279 |
| 5,609,635 | A | 3/1997 | Michelson |
| 5,645,596 | A | 7/1997 | Kim et al. |
| 5,658,337 | A * | 8/1997 | Kohrs et al. ................ 623/17.11 |
| 5,683,394 | A * | 11/1997 | Rinner ......................... 606/86 R |
| 6,371,988 | B1 | 4/2002 | Pafford et al. |

FOREIGN PATENT DOCUMENTS

| | | |
|---|---|---|
| EP | 0 599 419 | 6/1994 |
| FR | 2 710 519 | 4/1993 |
| FR | 93 11552 | 4/1995 |
| WO | WO 89/09035 | 10/1989 |
| WO | WO 90/00037 | 1/1990 |
| WO | WO 92/14423 | 9/1992 |
| WO | WO 94/26893 | 11/1994 |
| WO | WO 95/08306 | 3/1995 |
| WO | WO 9508306 A1 * | 3/1995 |
| WO | WO 95/31947 | 11/1995 |

OTHER PUBLICATIONS

The Treatment of Certain Cervical-Spine Disorders by Anterior Removal of the Intervertebral Disc and Interbody Fusion, George W. Smith, M.D., Robert A. Robinson, M.D., The Journal of Bone and Joint Surgery, vol. 40-A No. 3, Jun. 1958.

Product Literature: Cage CR "Cervical-Spacing Cages", Scient'x, 10 et 7, Rue Duvivier—75007, Paris.

Product Literature: Cage CH "Lumbar Spacing Cages", Scient'x, 10 et 7, Rue Duvivier—75007, Paris.

Proceedings, 10th Annual Conf. North American Spine Society, Oct. 18-21, 1995, Washington, D.C., pp. 10-11.

American Academy of Orthopaedic Surgeons 1996 Annual Meeting—Scientific Papers, discussion of papers 73, 74 and 75, Mark D. Brown, M.D., Miami, Florida.

Replacement of the Lumbar Vertebrae of Sheep w/Ceramic Prostheses, Takao Yamamuro, The Journal of Bone & Joint Surgery, vol. 72-B No. 5, Sep. 1990.

Healing Segmental Femoral Defects in Sheep Using Recombinant Human Bone Morphogenetic Protein, Tobin N. Gerhart, M.D. et al., Clinical Orthopaedics and Related Research, No. 293, pp. 317-326.

Preliminary Program from Forty-Second Annual Meeting of the Orthopaedic Research Society, Hyatt Regency, Atlanta, Georgia, Feb. 18-22, 1996.

* cited by examiner

INTERVERTEBRAL SPACERS

This application is a continuation of U.S. patent application Ser. No. 10/775,546 filed Feb. 10, 2004 now U.S. Pat. No. 7,311,734, which is a continuation of U.S. patent application Ser. No. 10/201,549 filed Jul. 23, 2002, now abandoned, which is a continuation of U.S. patent application Ser. No. 08/603,676 filed Feb. 20, 1996, now U.S. Pat. No. 6,423,095, which is a continuation-in-part of U.S. patent application Ser. No. 08/543,563 filed Oct. 16, 1995, now abandoned, the entire contents of each application hereby being incorporated by reference in their entirety.

FIELD OF THE INVENTION

The present invention broadly concerns devices for stabilizing the spine and devices for implantation between vertebrae, and more particularly in the intradiscal space. Specifically, the invention concerns hollow intervertebral spacers.

BACKGROUND OF THE INVENTION

Intervertebral discs, located between the end-plates of adjacent vertebrae, stabilize the spine, distribute forces between vertebrae and cushion vertebral bodies. A normal intervertebral disc includes a semi-gelatinous component, the nucleus pulposus, which is surrounded and confined by an outer, fibrous ring called the annulus fibrosus. In a healthy, undamaged spine, the annulus fibrosus prevents the nucleus pulposus from protruding outside the disc space.

Spinal discs may be displaced or damaged due to trauma, disease or aging. Disruption of the annulus fibrous allows the nucleus pulposus to protrude into the vertebral canal, a condition commonly referred to as a herniated or ruptured disc. The extruded nucleus pulposus may press on the spinal nerve, which may result in nerve damage, pain, numbness, muscle weakness and paralysis. Intervertebral discs may also deteriorate due to the normal aging process or disease. As a disc dehydrates and hardens, the disc space height will be reduced leading to instability of the spine, decreased mobility and pain.

Sometimes the only relief from the symptoms of these conditions is a discectomy, or surgical removal of a portion or all of an intervertebral disc followed by fusion of the adjacent vertebrae. The removal of the damaged or unhealthy disc will allow the disc space to collapse. Collapse of the disc space can cause instability of the spine, abnormal joint mechanics, premature development of arthritis or nerve damage, in addition to severe pain.

Bone grafts are often used to fill and preserve the intervertebral space and promote fusion. For example, in the Smith-Robinson technique of cervical fusion, the surgeon prepares the end-plates of the adjacent vertebral bodies to accept a graft after the disc has been removed. The end-plates are generally prepared to be parallel surfaces with a high speed burr. The surgeon sculpts the graft to fit tightly between the bone surfaces so that the graft is held by compression between the vertebral bodies. The bone graft is intended to provide structural support and promote bone ingrowth to achieve a solid fusion of the affected joint.

Unfortunately, the use of bone grafts presents several disadvantages. Autografts, bone material surgically removed from the patient, can be undesirable because they may not yield a sufficient quantity of graft material. The additional surgery to extract the autograft also increases the risk of infection and blood loss. Moreover, the structural integrity at the donor site can be reduced. Furthermore, some patients complain that the graft harvesting surgery is more painful than the fusion surgery.

Allograft material, which is obtained from donors of the same species, is more readily obtained. However, allografts can be disadvantageous because of the risk of disease transmission, immune reactions and religious objections. Furthermore, allogenic bone does not have the osteoinductive potential of autogenous bone and therefore may provide only temporary support.

Both allograft and autograft present additional difficulties. Graft alone may not provide the stability required to withstand spinal loads. Internal fixation may prevent graft collapse but presents its own disadvantages such as the need for more complex surgery. Also, the surgeon is often required to repeatedly trim the graft material to obtain the correct size to fill and stabilize the disc space. This trial and error approach increases the length of time required for surgery. Furthermore, the graft material usually has a smooth surface which does not provide a good friction fit between the adjacent vertebrae. Slippage of the graft may cause neural and vascular injury as well as collapse of the disc space.

Prosthetic implants can be used to prevent collapse of the space. The implant must provide temporary support and allow bone ingrowth. Success of the discectomy and fusion procedure requires the development of a contiguous growth of bone to create a solid mass because the implant may not withstand the compressive loads on the spine for the life of the patient.

A need has remained for fusion devices that preserve the intradiscal space and support the vertebral column until the adjacent vertebrae are fused yet still encourage bone ingrowth to achieve a solid fusion. A need has also remained for devices which reduce the length of surgical procedures and the risk of complications.

SUMMARY OF THE INVENTION

In accordance with the invention, hollow spinal spacers having anatomically friendly shapes and features are provided for engagement between vertebrae. The spacers are sized and configured to fill a space between adjacent vertebrae and include an anterior wall having opposite ends, a posterior wall having opposite ends, and two lateral walls. The lateral walls are each connected between the opposite ends of the anterior and posterior walls to define a chamber. The walls also define a superior face having a first opening which is in communication with the chamber and an opposite inferior face having a second opening which is also in communication with the chamber. The superior and inferior faces each define vertebral engaging surfaces. In one specific embodiment, the spacer is D-shaped having a basic flat geometry and a convexly curved anterior surface on the anterior wall. The flat spacer provides a friction fit by virtue of roughened vertebral engaging surfaces. In another specific embodiment, the implant is smile-shaped, having a radius in the superior and inferior faces which match the shape of vertebral end-plates. In another aspect of this invention, spacers include a biconvex shape in addition to a smile contour. In still a further aspect of this invention, spacers are provided with vertebral engaging surfaces that include blades for driving into the bone. In another specific embodiment, hollow spacers of this invention include lateral wings which are extendable into the disc space to prevent significant subsidence of the implant into the vertebral bodies.

One object of the invention is to provide an implant for engagement between vertebrae which restores the intervertebral disc space and supports the vertebral column while promoting bone ingrowth. Another object of the present invention is to provide spinal spacers which avoid the problems associated with allograft and autograft, such as the need for trial and error trimming of graft material to fit the intradiscal space, donor site morbidity and disease transmission risks.

One benefit of the implants of the present invention is that they provide structure for the space resulting from the removal of an intervertebral disc without the need for invasive autograft harvesting, allograft complications or internal fixation. Other objects and further benefits of the present invention will become apparent to persons of ordinary skill in the art from the following written description and accompanying figures.

DESCRIPTION OF THE PREFERRED EMBODIMENTS

Figure 1:
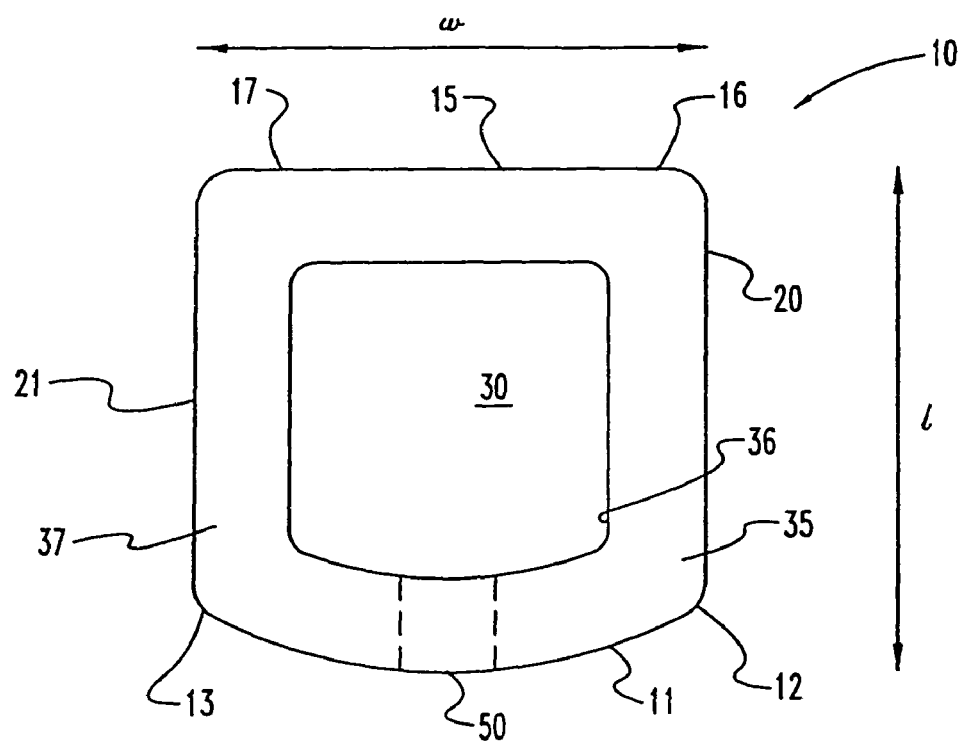
FIG. 1 is a top elevational view of a D-shaped spinal spacer according to one embodiment of this invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated devices, and such further applications of the principles of the invention as illustrated therein being contemplated as would normally occur to one skilled in the art to which the invention relates.

The present invention provides hollow spinal spacers for engagement between vertebrae which are sized and configured to fill the space left after discectomy. The inventive spacers restore height of the intervertebral disc space and provide immediate load bearing capability and support for the vertebral column without internal fixation. This invention eliminates the need for invasive autograft harvesting and trial and error trimming of graft material to fit the intradiscal space. The implants advantageously have anatomically friendly shapes and features which increase stability and decrease the risk of complications.

Figure 2:
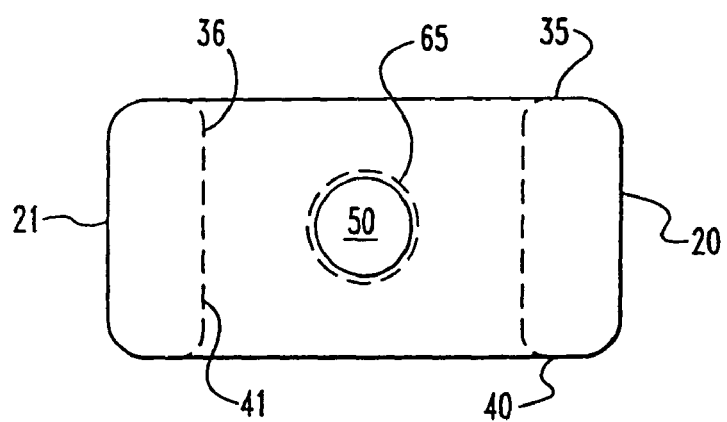
FIG. 2 is an anterior elevational view of a hollow spacer having a basic flat geometry.
Figure 3:
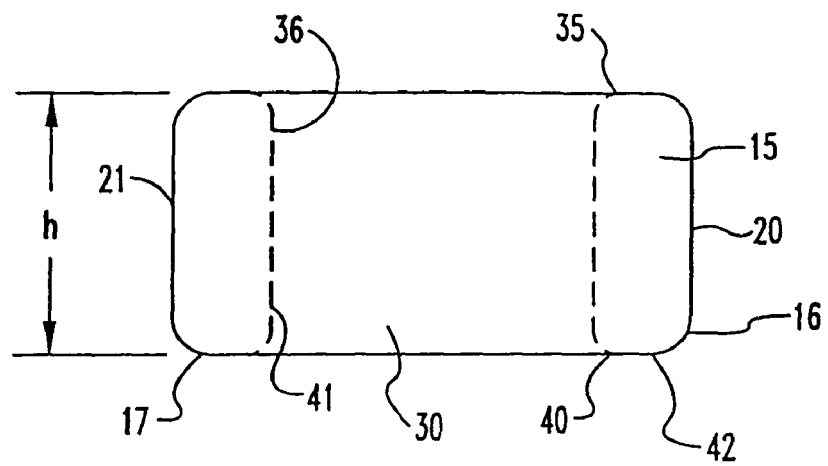
FIG. 3 is a posterior elevational view of the spacer depicted in FIG. 2.

A spacer 10 for engagement between the vertebrae in accordance with a preferred embodiment of the present invention is depicted in FIGS. 1-3. The spacer 10 includes an anterior wall 11 having opposite ends 12, 13, a posterior wall 15 having opposite ends 16, 17 and two lateral walls 20, 21. Each of the lateral walls 20, 21 are connected between the opposite ends 12, 13, 16, 17 of the anterior 11 and posterior 15 walls to define a chamber 30. The walls also define the superior face 35 which defines a first opening 36 in communication with the chamber 30. The superior face 35 includes a first vertebral engaging surface 37. As shown in FIGS. 2 and 3 the walls further define an opposite inferior face 40 defining a second opening 41 which is in communication with the chamber 30. The inferior face 40 includes a second vertebral engaging surface (not shown) which is similar or identical to the first vertebral engaging surface.

The present invention provides several anatomically compatible and surgically convenient features which reduce the risk of complications during and after implantation. In one specific embodiment for an intervertebral disc replacement implant, a hollow D-shaped spinal spacer is provided. The anterior wall 11 as shown in FIGS. 1-3 is convexly curved. This anterior curvature is preferred to conform to the geometry of the harder cortical bone of the adjacent vertebral bodies. The D-shape of the spacer 10 prevents any extension of the edges of the anterior wall 11 outside the anterior aspect of the disc space, which can be particularly important for spacers implanted in the cervical spine to avoid impinging on soft tissues.

Figure 4:
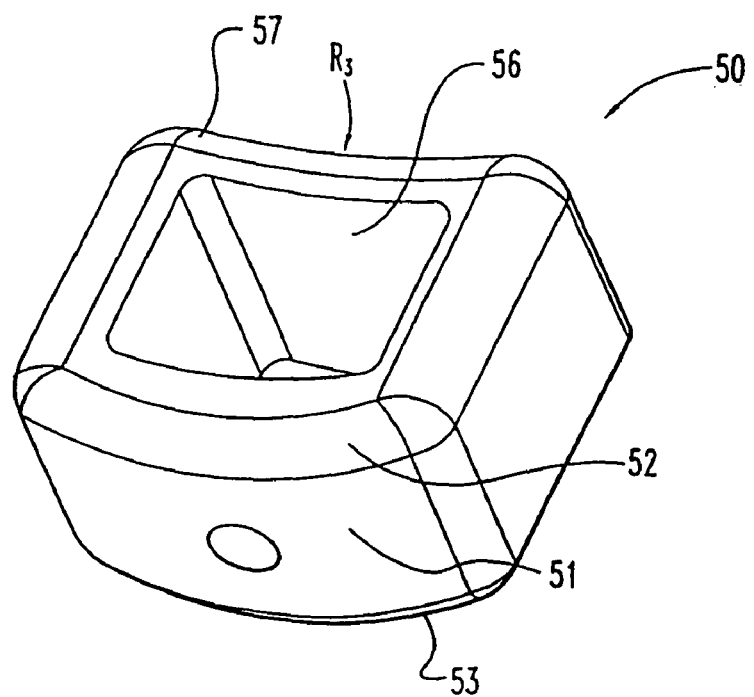
FIG. 4 is a perspective view of a smile-shaped implant of this invention.
Figure 5:
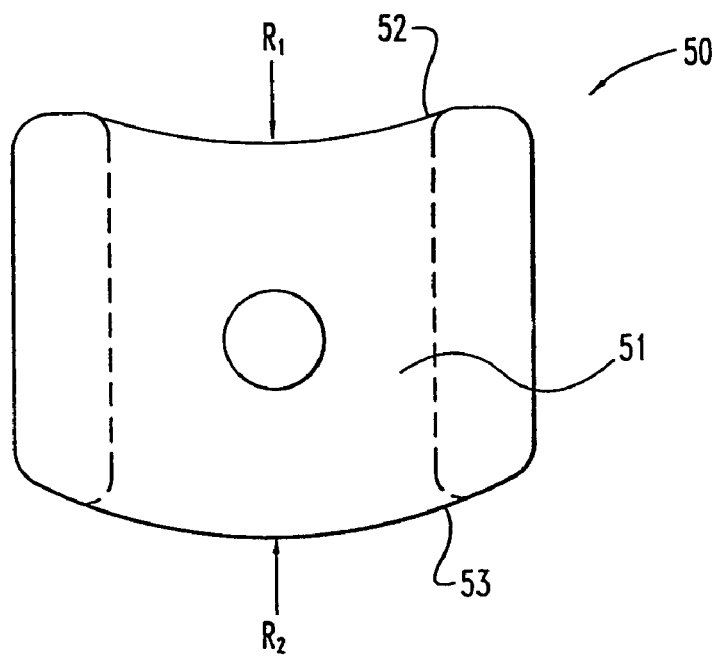
FIG. 5 is an anterior elevational view of the implant depicted in FIG. 4.

In another specific embodiment, the spacer is smile-shaped. The superior and inferior faces are each equipped with a radius that corresponds to the shape of the adjacent vertebral end-plates. Referring to FIGS. 4 and 5, the anterior wall 51 of the spacer 50 defines an anterior superior surface 52 and an anterior inferior surface 53 (so identified due to their anatomic position when the spacers are implanted). The posterior wall 56 of the spacer 50 defines a posterior superior surface 57 and a posterior inferior surface (not shown). The anterior superior surface 52 has a concave shape defining a first radius $R_1$ which is configured to conform to the anterior shape of an inferior vertebral end-plate. The anterior inferior surface 53 also has a concave shape defining a second radius $R_2$ which is configured to correspond to the anterior shape of a superior vertebral end-plate. Preferably, the posterior portions of the spacer are also similarly curved, the posterior superior surface 57 defining a third radius $R_3$ configured to correspond to the posterior shape of an inferior vertebral end-plate and the posterior inferior surface defining a fourth radius (not shown) configured to correspond to the posterior shape of a superior vertebral end-plate. Each of the radii preferably range between about 0.500" and about 1.250" for use in the cervical spine. Most preferably each of the radii are about 0.750. This smile shaped embodiment is more end-plate preserving than flat implants and provides rotational stability to the spacer 50.

Figure 6:
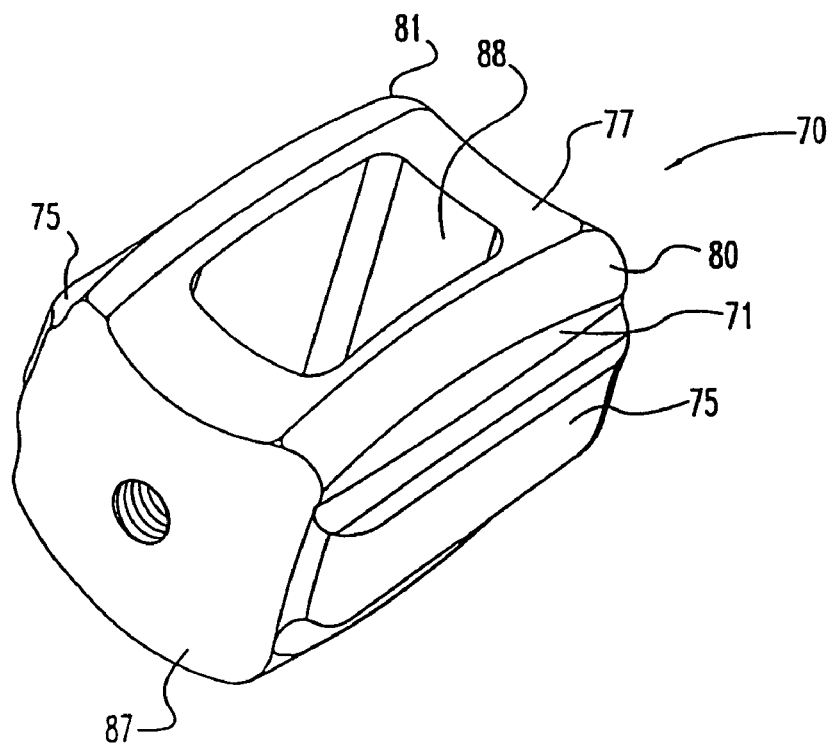
FIG. 6 is a perspective view of a spacer having a biconvex shape and lateral wings according to one embodiment of this invention.
Figure 7:
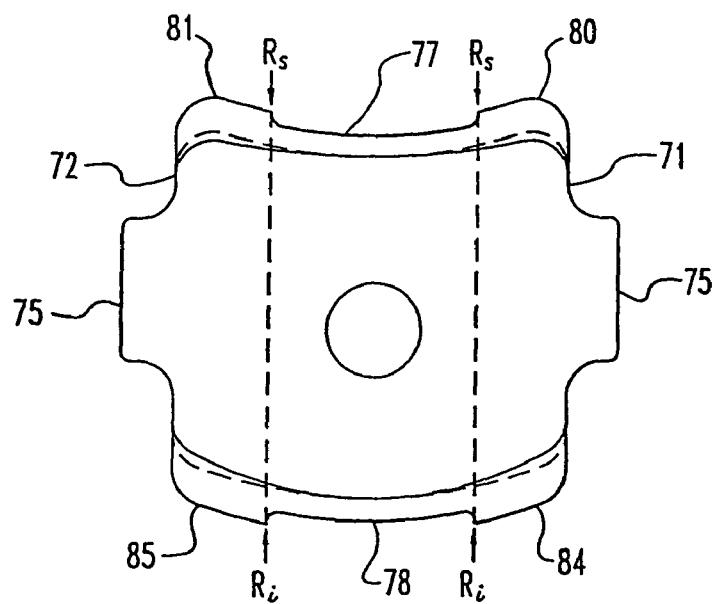
FIG. 7 is an anterior elevational view of the spacer depicted in FIG. 11.

The invention also contemplates biconvex embodiments which are anatomically friendly and increase stability. One example of a biconvex spacer is shown in FIGS. 6-9. The lateral walls 71, 72 of the spacer 70 each define a convex lateral superior surface 80, 81 and a convex lateral inferior surface 84, 85. Each of the lateral superior surfaces 80, 81 defines a superior radius R configured to conform to the inferior shape of a vertebral end-plate. Likewise, each of the lateral inferior surfaces 84, 85 define an inferior radius $R_i$ configured to correspond to the superior shape of a vertebral end-plate. Preferably, the inferior $R_i$ and superior $R_s$ radii are each between about 0.500" and about 1.250" for use in the cervical spine. Most preferably, the inferior $R_i$ and superior $R_s$ radii are each about 0.75. The most preferred anatomically friendly spacer will combine a biconvex shape with a smile shape as shown in FIGS. 6 and 7.

Figure 10:
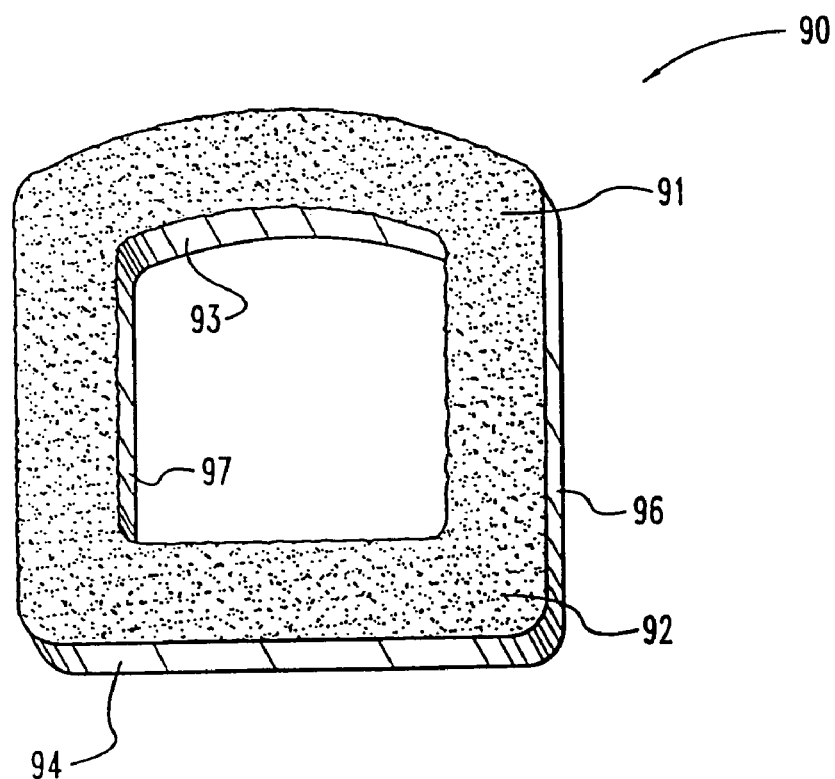
FIG. 10 is a top elevational view of a hollow D-shaped spacer having a roughened vertebral engaging surface.

In some embodiments, the spacers include vertebrae engaging means. Any suitable vertebrae engaging means is contemplated that provides sufficient frictional engagement with the vertebrae to prevent expulsion. For example, as shown in FIG. 10, the superior 91 and inferior (not shown) faces of the spacer 90 define a roughened surface 92 adapted to provide a friction fit with the adjacent vertebrae. The roughened vertebral engaging surfaces 92 may be produced by rough grit sand blasting or shot peening techniques. Preferably, the anterior 93, posterior 94 and lateral 96, 97 walls are masked during the sand blasting so that they remain smooth.

Figure 11:
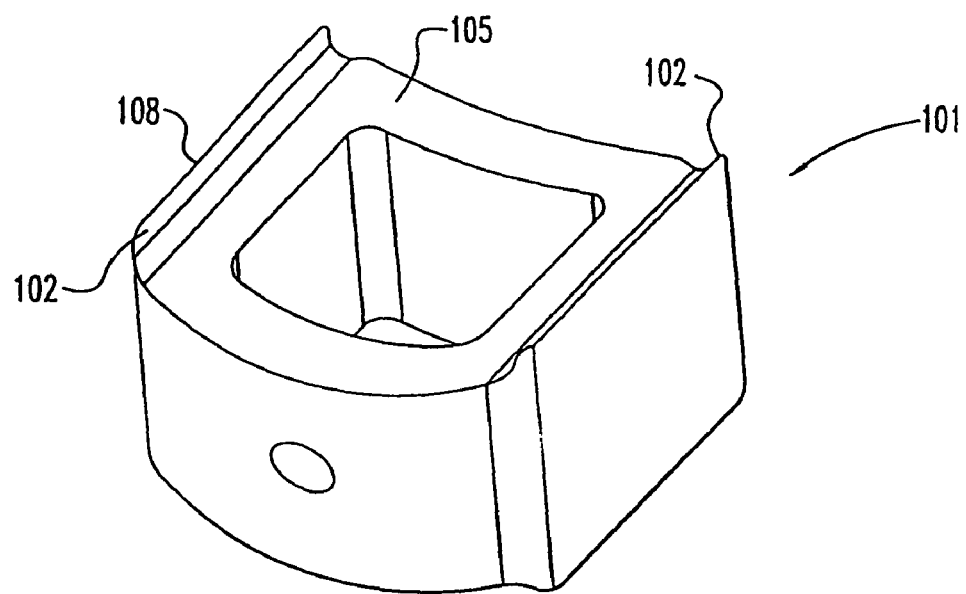
FIG. 11 is a top perspective view of an implant having blades.
Figure 12:
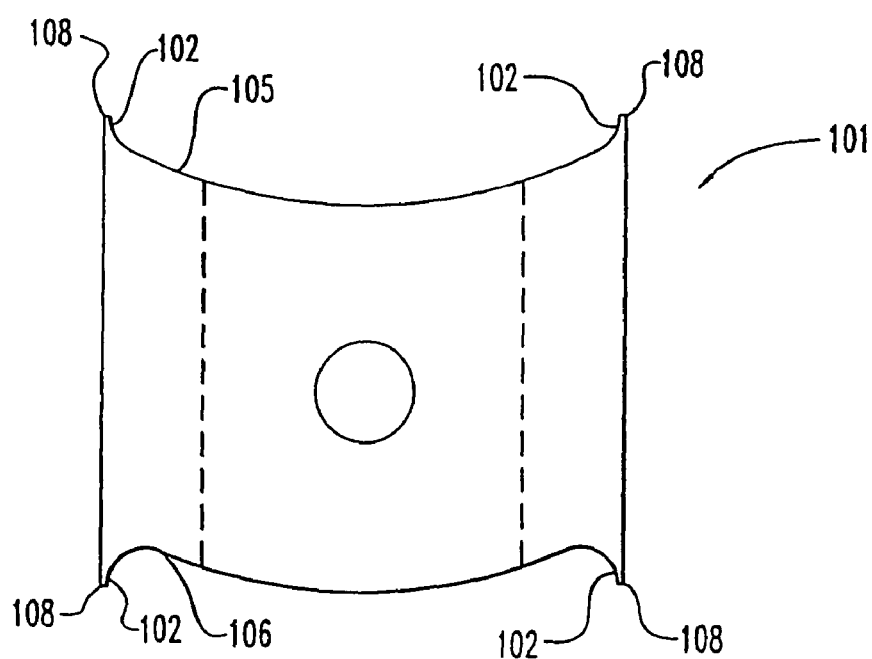
FIG. 12 is an anterior elevational view of the implant depicted in FIG. 11.

Other vertebrae engaging means for spacers of this invention are blade members which extend from either or both of the engaging faces. The spacer 101 shown in FIGS. 11 and 12 includes a pair of blades 102 extending from the superior 105 and inferior 106 faces. The blades 102 each include a cutting edge 108 configured to pierce a vertebral end-plate. The blades 102 can be driven into the bone surface to increase the initial stability of the device.

The stability of the fusion site can also be increased with the wing feature. Referring to FIGS. 6-9, the spacer 70 includes lateral wings 75 projecting from an external surface of each of the lateral walls 71, 72. Preferably the wings are disposed between the superior 127 and inferior 78 faces. Most preferably, the lateral wings 75 each extend from the anterior wall 87 to the posterior wall 88. This wing feature provides added stability to intervertebral spacers which can be particularly important when the end-plates are weak. One complication that can arise when the end-plates are weak are that the fusion device may sink or subside into the vertebral body, allowing the disc space to collapse. The lateral wings 75 extend into the disc space and contact the bone if subsidence occurs to prevent any further subsidence. The invention contemplates that the walls of the spacer will be of a sufficient thickness to provide structural support. In one specific embodiment for use in the cervical spine, the walls were each about 2 mm thick.

The spacers 10 of this invention are also preferably shaped to be conveniently and efficiently incorporated into current surgical techniques. For example, a spacer of this invention having a flat posterior wall is easily incorporated into a Smith Robinson surgical fusion technique. See, for example, Smith, M. D., G. W. and Robinson, M. D., R. A., "The Treatment of Certain Cervical-Spine Disorders By Anterior Removal Of The Intervertebral Disc And Interbody Fusion", *J. Bone And Joint Surgery*, 40-A:607-624 (1958) and Cloward, M. D., R. B., "The Anterior Approach For Removal Of Ruptured Cervical Disks", in meeting of the Harvey Cushing Society, Washington, D.C., Apr. 22, 1958. After total or partial discectomy and distraction, the surgeon prepares the end plates for the spacer 10, preferably to create flat posterior and lateral edges. The spacer 10 (FIG. 1) fits snugly with its flat surfaces against the posterior and lateral edges which prevents medial and lateral motion of the spacer 10 into vertebral arteries and nerves. This also advantageously reduces the time required for the surgery by eliminating the trial and error approach to achieving a good fit with bone grafts. Normally, the surgeon is required to repeatedly whittle away the graft to obtain the correct size to fit in the intervertebral space.

The intervertebral spacers of the present invention do not require internal fixation. The spacers are contained by the compressive forces of the surrounding ligaments and muscles. Temporary external immobilization and support is generally recommended until adequate fusion is achieved. For example, a cervical collar is recommended when the spacer is implanted in the cervical spine.

Figure 8:
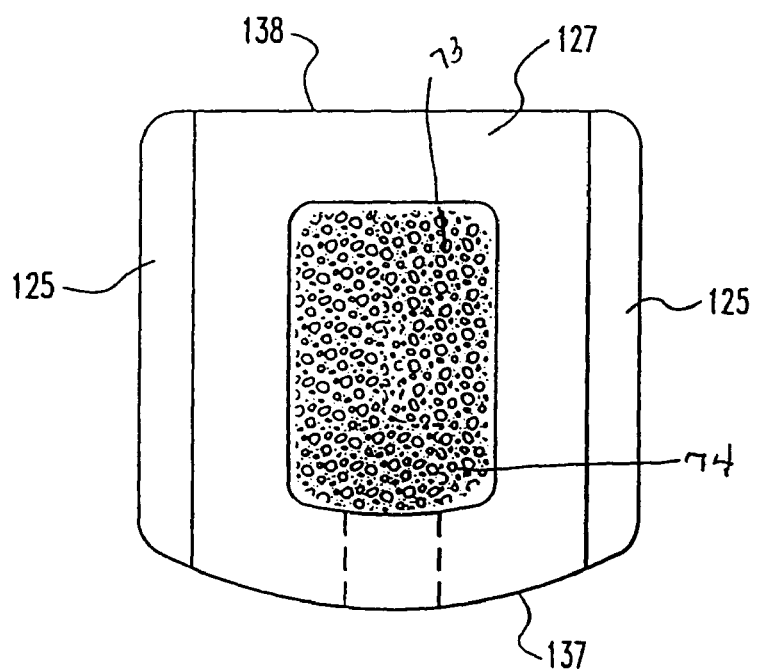
FIG. 8 is a top elevational view of the spacer depicted in FIGS. 6 and 7 showing an osteoinductive m.
Figure 9:
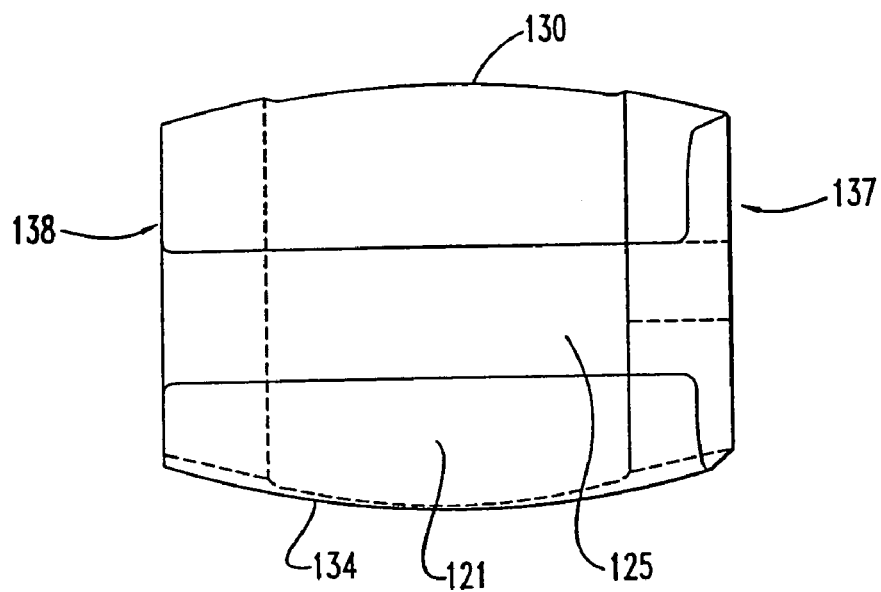
FIG. 9 is a side elevational view of the spacer depicted in FIGS. 6-9.

During the fusion procedure, the surgeon may pack the chamber 30 with an osteogenic material 73 as shown in FIG. 8. The osteogenic material preferably is an osteoinductive material such as autograft, certain bioceramics or bone osteogenic proteins such as bone morphogenic proteins (BMPs), all of which are well known in the art. The chamber 30 may also be packed with an osteoconductive material such as allograft or certain bioceramics. All suitable osteogenic materials are contemplated. Bioceramics may include biphasic calcium phosphate ceramics such as hydroxyapatite/tricalcium phosphate ceramics which are commercially available.

The osteogenic material may be autograft or allograft, including osteocytes or other bone reamed away by the surgeon while preparing the end plates for the spacer or morcellized bone graft from a bone bank or autograft, for example from the iliac crest.

Where BMPs are included in the osteoinductive material, the BMPs may be naturally obtained or genetically engineered BMPs. Most preferably, the bone morphogenic protein is a BMP-2, such as recombinant human BMP-2. However, any bone morphogenic protein is contemplated including but not limited to bone morphogenetic proteins designated as BMP-1 through BMP-13. Such BMPs are available from Genetics Institute, Inc., 87 Cambridge Park Drive, Cambridge, Mass. 02140, and may also be prepared by one skilled in the art as described in U.S. Pat. Nos. 5,187,076 to Wozney et al.; 5,318,898 to Israel; 5,166,058 to Wang et al.; 5,366,875 to Wozney et al.; 4,877,864 to Wang et al.; 5,108,922 to Wang et al.; 5,116,738 to Wang et al.; 5,013,649 to Wang et al.; 5,106,748 to Wozney et al.; and PCT Patent Nos. WO93/00432 to Wozney et al.; WO94/26893 to Celeste et al.; and WO94/26892 to Celeste et al which are hereby incorporated by reference.

The BMPs are preferably introduced into the chamber 30 with a suitable carrier 74 as shown in FIG. 8. The carrier may be any suitable medium capable of delivering the proteins to the implant. Such carriers are well known and commercially available. One preferred carrier is an absorbable collagen sponge as shown in FIG. 8 marketed by Integra LifeSciences Corporation under the trade name Helistat® Absorbable Collagen Hemostatic Agent. Another preferred carrier is an open cell polylactic acid polymer (OPLA). Other potential matrices for the compositions may be biodegradable and chemically defined calcium sulfate, tricalcium phosphate (TCP), hydroxyapatite (HA), biphasic TCP/HA ceramic, polylactic acids and polyanhydrides. Other potential materials are biodegradable and biologically well defined, such as bone or dermal collagen. Further matrices are comprised of pure proteins or extracellular matrix components. The osteoinductive material may also be an admixture of the osteoinductive cytokine and a polymeric acrylic ester carrier. The polymeric acrylic ester can be polymethylmethacrylic. The carriers are preferably provided in strips or sheets which may be folded to conform to the chamber 30.

The choice of carrier is based on biocompatibility, biodegradability, mechanical properties and interface properties. The particular application of the compositions of the invention will define the appropriate formulation. The carrier may be any suitable carrier capable of delivering the proteins to the spacer.

Advantageously, where graft is chosen as the osteogenic material, only a very small amount of bone material is needed. The graft itself is not required to provide structural support as this is provided by the spacer 10. Instead the graft is merely required for its osteoconductive and/or osteoinductive properties to promote fusion across the disc space. The donor surgery for such a small amount of bone is less invasive and better tolerated by the patient. There is little need for muscle dissection in obtaining such small amounts of bone. The present invention therefore eliminates many of the disadvantages of autograft.

The present invention increases the surgeon's efficiency in implanting the spacer. A thru-hole 50 is defined in the anterior wall 11 which is configured to receive an implanting tool. Any suitable tool is contemplated, such as the implant inserter 60 depicted in FIG. 13.

Figure 13:
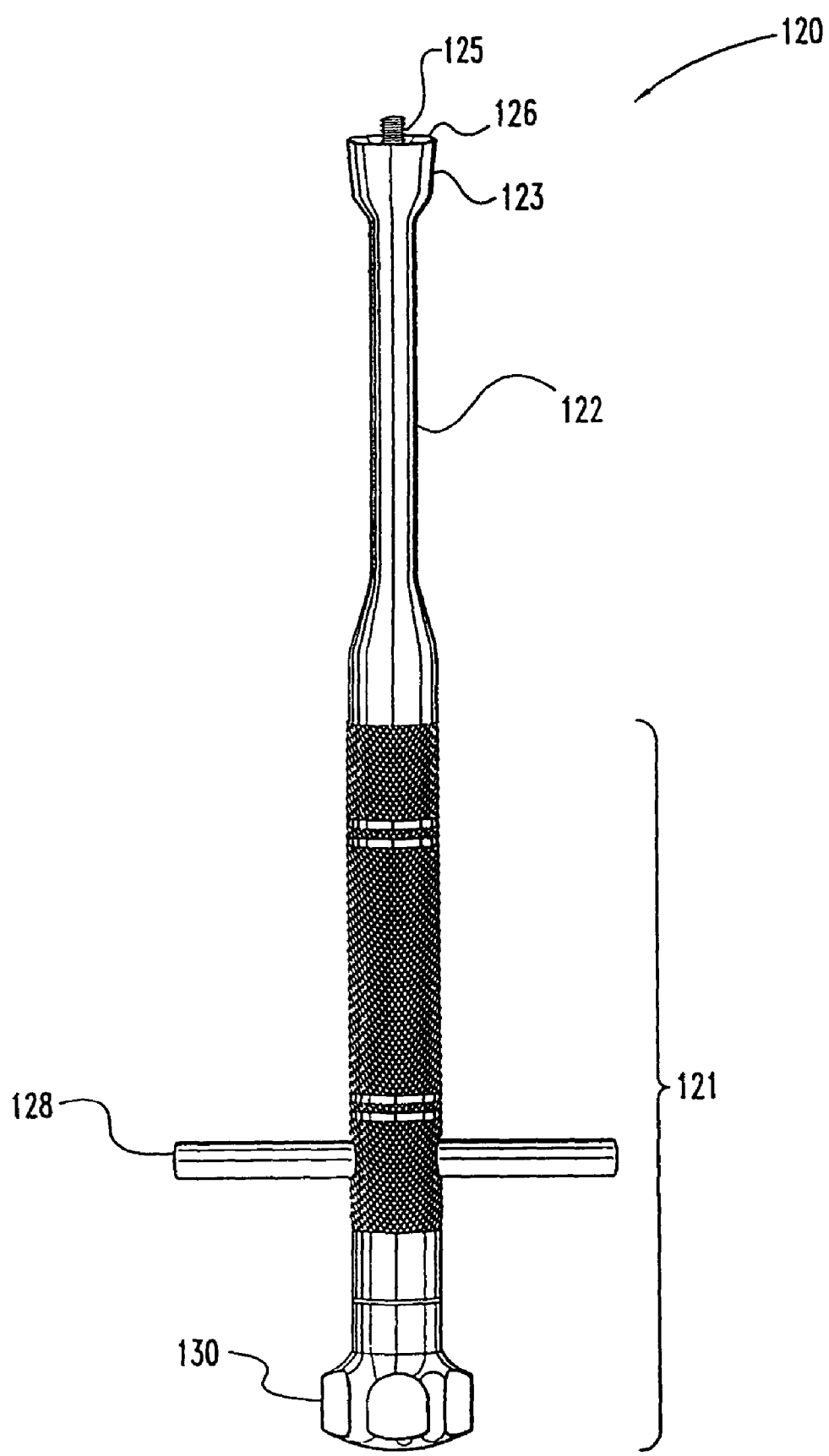
FIG. 13 depicts a tool which may be used to implant the spacers of this invention.

The inserter 120 includes a handle portion 121 with knurlings or other suitable patterns to enhance manual gripping of the handle. A shaft 122 extends from the handle 121. The distal end 123 of the shaft 122 includes a tip 125 which mates with the thru-hole 50. Preferably the tip 125 and thru-hole 50 have corresponding mating threads 126, 51. Where the thru-hole 50 is defined in a curved wall as shown in FIG. 1, the distal end 123 of the shaft 122 preferably includes a curved portion 124 that conforms to the curved anterior surface of the implant. The inserter 120 also preferably includes a T-handle 128 for implant control and positioning. Preferably the inserter 120 includes means for rotating the threaded tip 125. In FIG. 13, the knob 130 is engaged to the tip 125 via an inner shaft extending through an internal bore (not shown) in the handle 121 and shaft 122. The tip 125 is preferably at the end of the inner shaft with the inner shaft rotatingly mounted within the handle 121 and shaft 122.

In the use of the inserter 120, a spacer 10 is engaged to the threaded tip 125 with the curved portion 124 flush with the anterior wall 11. The inserter and spacer can then be extended percutaneously into the surgical site to implant the spacer in the intradiscal space. Once the spacer 10 is properly positioned, the knob 130 can be turned to rotate the threaded tip 125 and disengage the tip from the thru-hole 50 of the spacer 10. The inserter 120 can then be withdrawn from the surgical site leaving the spacer 10 in place.

Any suitable biocompatible material which can withstand high spinal loads is contemplated. The most preferred materials include titanium, stainless steel and certain biocomposites, such as the one described in U.S. Pat. No. 5,282,861 to Kaplan and marketed under the name of Hedrocel®. The Kaplan composite includes a nonmetallic rigid foam substrate defining continuous, interconnected pores and a metallic film substantially covering the interconnected network. The Kaplan material provides two important advantages: complete porosity and roughness. As discussed in the Kaplan patent, the open cell tantalum material provides highly interconnected three-dimensional porosity that encourages bone ingrowth. Because the material of the spacer itself is porous and supports bone ingrowth, there is no need for extra machining of open side slots. This material also provides an unexpected benefit in that the roughness of the surface provides a friction fit between the vertebral bodies.

Any suitably sized spacer is contemplated. Preferably the spacer 10 has a height h (FIG. 3) approximating the height of a particular human disc space. In some applications, it may be preferable that the height of the spacer 10 be slightly larger than the height of a human disc space to preserve disc space height under the compressive forces of the spine and to avoid the effects of subsidence and bone erosion. In cervical applications, some specific embodiments have a height from about 6 mm to about 10 mm. In other specific embodiments for use in the cervical spine, spacers have a width (w) (FIG. 1) of between about 10 mm to about 14 mm and a length (l) of between about 10 to about 14 mm. The invention contemplates that the walls of the spacer will be of sufficient thickness to provide structural support. In one specific embodiment for use in a cervical spine, the walls were each about 2 mm thick. Appropriately sized thoracic and lumbar spacers are also contemplated to be used with appropriate surgical techniques.

This invention provides implants for engagement between vertebrae which restore the intervertebral disc space and supports the vertebral column while promoting bone ingrowth. The spacers are anatomically friendly and provide a vehicle for osteogenic or osteoconductive material. The implants of this invention avoid the problems associated with allograft and autograft, such as the need for trial and error trimming of graft material to fit the intradiscal space, donor site morbidity and disease transmission risks.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A hollow spinal spacer for engagement within an intervertebral space between adjacent vertebrae, comprising:
    an anterior wall;
    a posterior wall;
    two lateral walls integrally connected between said anterior and posterior walls to define a monolithic, single-piece spacer body having a hollow inner chamber defined by said walls;
    wherein said lateral walls each have a flat lateral surface extending continuously from said anterior wall to said posterior wall;
    said spacer body sized and shaped to substantially fill the intervertebral space between the adjacent vertebrae such that a single spacer body is sufficient to preserve a height of the intervertebral space; and
    said spacer body defining a superior vertebral engaging face and an opposite inferior vertebral engaging face, said superior vertebral engaging face defined by a thickness of said walls extending about and defining a first superior opening in communication with said chamber, said inferior vertebral engaging face defined by a thickness of said walls extending about and defining a second inferior opening in communication with said chamber;
    wherein the spacer defines an overall spacer width between said lateral walls and an overall spacer length between said anterior wall and said posterior wall;
    wherein a concave outer surface curvature is defined by one of said superior vertebral engaging face and said inferior vertebral engaging face and extends along the overall spacer length; and wherein an opposite one of said superior vertebral engaging face and said inferior vertebral engaging face defines a convex outer surface curvature extending laterally between said lateral walls and extending along the overall spacer length.

2. The spacer of claim 1, wherein said anterior wall has a convexly curved anterior surface sized and shaped to substantially conform to an anterior aspect of the adjacent vertebrae, and wherein said posterior wall has a flat posterior surface.

3. The spacer of claim 2, wherein at least one of said lateral walls defines an outer surface curvature extending from said anterior wall to said posterior wall.

4. The spacer of claim 3, wherein said outer surface curvature extends continuously from said anterior wall to said posterior wall.

5. The spacer of claim 3, wherein said lateral wall outer surface curvature comprises a convex curvature.

6. The spacer of claim 5, wherein said convex curvature extends continuously from said anterior wall to said posterior wall.

7. The spacer of claim 3, wherein said lateral wall outer surface curvature is defined by said superior and inferior vertebral engaging faces of said lateral walls.

8. The spacer of claim 2, wherein said lateral walls each have a flat lateral surface extending continuously from said anterior wall to said posterior wall to provide said spacer body with a D-shape.

9. The spacer of claim 1, wherein at least one of said anterior wall and said posterior wall defines an outer surface curvature extending between said lateral walls.

10. The spacer of claim 9, wherein said outer surface curvature comprises a convex curvature defined by an anterior surface of said anterior wall and sized and shaped to substantially conform to an anterior aspect of an adjacent vertebra, and wherein said posterior wall has a flat posterior surface.

11. The spacer of claim 1, wherein at least one of said superior vertebral engaging face and said inferior vertebral engaging face defines at least one surface curvature that substantially conforms to a contour of an adjacent vertebral endplate.

12. The spacer of claim 11, wherein said surface curvature comprises a convex curvature.

13. The spacer of claim 12, wherein said convex curvature is defined by each of said lateral walls and extends between said anterior and posterior walls.

14. The spacer of claim 13, wherein said convex curvature extends continuously between said anterior and posterior walls.

15. The spacer of claim 12, wherein said convex curvature is defined by at least one of said anterior and posterior walls and extends between said lateral walls.

16. The spacer of claim 15, wherein said convex curvature extends continuously between said lateral walls.

17. The spacer of claim 11, wherein said anterior wall has a convexly curved anterior surface sized and shaped to substantially conform to an anterior aspect of the adjacent vertebrae;
wherein said posterior wall has a flat posterior surface; and
wherein said lateral walls each have a substantially flat lateral surface extending continuously from said anterior wall to said posterior wall.

18. The spacer of claim 1, wherein said anterior wall defines a threaded opening extending therethrough configured for engagement with an implanting tool to allow for anterior insertion of the spinal spacer into the intervertebral space between the adjacent vertebrae.

19. A hollow spinal spacer for
engagement within an intervertebral space between adjacent vertebrae, comprising:
an anterior wall;
a posterior wall;
two lateral walls integrally connected between said anterior and posterior walls to define a monolithic, single-piece spacer body having a hollow inner chamber defined by said walls;
said spacer body sized and shaped to substantially fill the intervertebral space between the adjacent vertebrae such that a single spacer body is sufficient to preserve a height of the intervertebral space; wherein said spacer body defines an overall spacer length between said anterior wall and said posterior wall;
said spacer body defining a superior vertebral engaging face and an opposite inferior vertebral engaging face, said superior vertebral engaging face defined by a thickness of said walls extending about and defining a first superior opening in communication with said chamber, said inferior vertebral engaging face defined by a thickness of said walls extending about and defining a second inferior opening in communication with said chamber;
wherein said lateral walls each have a substantially flat lateral surface extending continuously from said anterior wall to said posterior wall;
wherein at least one of said anterior wall and said posterior wall defines an outer surface curvature extending between said lateral walls; and
wherein said outer surface curvature comprises a concave curvature extending between said lateral walls;
wherein said concave curvature is defined by one of said superior vertebral engaging face and said inferior vertebral engaging face and extends along the overall spacer length; and wherein an opposite one of said superior vertebral engaging face and said inferior vertebral engaging face defines a convex outer surface curvature extending laterally between said lateral walls and extending along the overall spacer length.

20. The spacer of claim 19, wherein said concave curvature extends continuously between said lateral walls.

21. The spacer of claim 19, wherein said concave curvature is defined by said posterior wall and is sized and shaped to substantially conform to a posterior aspect of an adjacent vertebra.

22. The spacer of claim 21, wherein said concave curvature is defined by said superior vertebral engaging face of said posterior wall.

23. The spacer of claim 19, wherein the spacer defines an overall spacer width between said lateral walls, said overall spacer width being substantially equal to said overall spacer length.

24. A hollow spinal spacer for engagement within an intervertebral space between adjacent vertebrae, comprising:
an anterior wall;
a posterior wall;
two lateral walls integrally connected between said anterior and posterior walls to define a monolithic, single-piece spacer body having a hollow inner chamber defined by said walls;
wherein said lateral walls each have a substantially flat lateral surface extending continuously from said anterior wall to said posterior wall;
wherein said spacer body defines an overall spacer length between said anterior wall and said posterior wall;
said spacer body sized and shaped to substantially fill the intervertebral space between the adjacent vertebrae such that a single spacer body is sufficient to preserve a height of the intervertebral space; and
said spacer body defining a superior vertebral engaging face and an opposite inferior vertebral engaging face, said superior vertebral engaging face defined by a thickness of said walls extending about and defining a first superior opening in communication with said chamber, said inferior vertebral engaging face defined by a thickness of said walls extending about and defining a second inferior opening in communication with said chamber;
wherein at least one of said superior vertebral engaging face and said inferior vertebral engaging face defines at least one surface curvature that substantially conforms to a contour of an adjacent vertebral endplate; wherein said surface curvature comprises a concave curvature that extends along the overall spacer length; and
wherein an opposite one of said superior vertebral engaging face and said inferior vertebral engaging face defines a convex outer surface curvature extending laterally between said lateral walls and extending along the overall spacer length.

25. The spacer of claim 24, wherein said concave curvature is defined by at least one of said anterior and posterior walls and extends between said lateral walls.

26. The spacer of claim 25, wherein said concave curvature extends continuously between said lateral walls.

27. The spacer of claim 24, wherein the spacer defines an overall spacer width between said lateral walls, said overall spacer width being substantially equal to said overall spacer length.

* * * * *